United States Patent
Griffiths et al.

(10) Patent No.: US 7,145,007 B2
(45) Date of Patent: Dec. 5, 2006

(54) PROCESS FOR THE PREPARATION OF (PYRIMIDIN-2-YL) METHYL KETONES

(75) Inventors: Gareth J. Griffiths, Visp (CH); Hidetaka Hiyoshi, Nakanogo (JP)

(73) Assignees: Lonza Ltd., Basel (CH); Ihara Chemical Industry Co. Ltd., Shizuoka (JP)

(*) Notice: Subject to any disclaimer, the term of this patent is extended or adjusted under 35 U.S.C. 154(b) by 483 days.

(21) Appl. No.: 10/491,186

(22) PCT Filed: Oct. 9, 2002

(86) PCT No.: PCT/EP02/11279

§ 371 (c)(1),
(2), (4) Date: Mar. 31, 2004

(87) PCT Pub. No.: WO03/033474

PCT Pub. Date: Apr. 24, 2003

(65) Prior Publication Data

US 2004/0242876 A1  Dec. 2, 2004

(30) Foreign Application Priority Data

Oct. 17, 2001  (EP)  .................... 01124728

(51) Int. Cl.
*C07D 239/52* (2006.01)
*C07C 251/08* (2006.01)

(52) U.S. Cl. .................................... 544/319
(58) Field of Classification Search .............. 544/319
See application file for complete search history.

(56) References Cited

U.S. PATENT DOCUMENTS 5,276,152 A  1/1994  Escher et al.

OTHER PUBLICATIONS

Eilingsfeld, H., et al., Chemische Berichte, vol. 101, (1968), pp. 2426-2434.

*Primary Examiner*—Deepak Rao
(74) *Attorney, Agent, or Firm*—Fisher Christen & Sabol

(57) ABSTRACT

A process for the preparation, of (pyrimidin-2-yl)methyl ketones of the general formula (I),

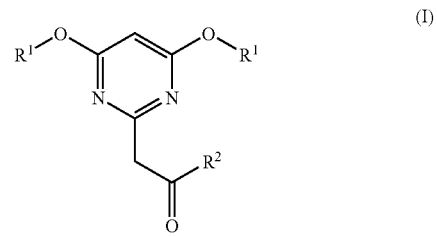

in which $R^1$ is in each case a $C_{1-10}$-alkyl group, a $C_{3-8}$-cycloalkyl group, an allyl group or an aryl-$C_{1-4}$-alkyl group, and $R^2$ is a $C_{1-10}$-alkyl group or aryl group. For this, a malondiimidate of the general formula (II),

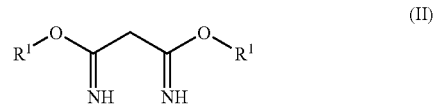

in which $R^1$ has the meaning given above, is reacted with a β-keto ester of the general formula (III),

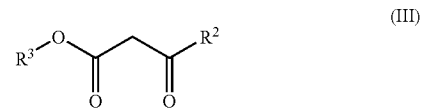

in which $R^2$ has the meaning given above, and $R^3$ is a $C_{1-10}$-alkyl group. The compounds which can be prepared according to the invention are intermediates for the synthesis of agrochemical active ingredients.

13 Claims, No Drawings

PROCESS FOR THE PREPARATION OF (PYRIMIDIN-2-YL) METHYL KETONES

This is a 371 national stage application of International Patent Application No. PCT/EP02/11279, filed on Oct. 9, 2002, that has priority benefit of European Patent Application No. 01124728.5, filed on Oct. 17, 2001.

The invention relates to a process for the preparation of (pyrimidin-2-yl)methyl ketones of the general formula

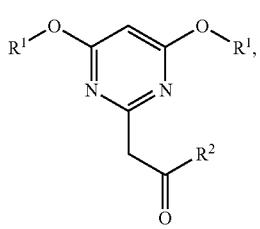

in which $R^1$ is in each case a $C_{1-10}$-alkyl group, a $C_{3-8}$-cycloalkyl group, an allyl group or an aryl-$C_{1-4}$-alkyl group, and $R^2$ is a $C_{1-10}$-alkyl group or aryl group. $C_{1-10}$-Alkyl groups are understood here and below as meaning all linear or branched primary, secondary or tertiary alkyl groups having 1 to 10 carbon atoms, thus, for example, methyl, ethyl, propyl, isopropyl, butyl, isobutyl, sec-butyl, tert-butyl, pentyl, isopentyl, tert-pentyl, neopentyl, hexyl, heptyl, octyl, nonyl or decyl.

$C_{3-8}$cycloalkyl are to be understood as meaning, in particular, cyclopropyl, cyclobutyl, cyclopentyl, cyclohexyl, cycloheptyl and cyclooctyl.

Aryl-$C_{1-4}$-alkyl groups are the groups composed of an aryl group and an alkyl group having 1 to 4 carbon atoms, aryl groups being understood as meaning, in particular, phenyl or naphthyl groups. The aryl groups may also be substituted by one or more $C_{1-4}$-alkyl groups, $C_{1-4}$-alkoxy groups or halogen atoms. Examples of aryl-$C_{1-4}$-alkyl groups are, in particular, benzyl, 1-phenylethyl, 2-phenylethyl and 3-phenylpropyl.

Compounds of the formula I, in particular 1-(4,6-dimethoxypyrimidin-2-yl)propan-2-one ($R^1=R^2=Me$) are potential intermediates in the synthesis of agrochemical active ingredients.

Syntheses of these compounds have hitherto not been described in the prior art.

It was an object of the present invention to provide a preparation process which is simple and suitable for an industrial scale.

According to the invention, the object is achieved by the process of the invention. It has been found that the malondiimidate, which are readily available from malodinitrile and the corresponding alcohols (DE-A-24 26 913, EP-A-0 024 200), of the general formula:

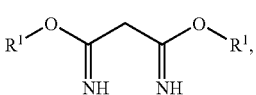

in which $R^1$ has the meaning given above, react with β-keto esters of the general formula:

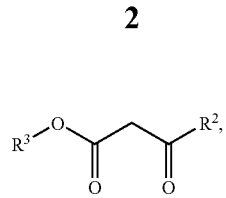

in which $R^2$ has the meaning given above, and $R^3$ is a $C_{1-10}$-alkyl group, directly and in a good yield to give the desired compounds (I).

The reaction is advantageously carried out in such a way that the water formed during the reaction is removed from the reaction mixture. This can be achieved, for example, by adding a dehydrating agent or by azeotropic distillation with a suitable entrainer.

The malondiimidates (II) can either be used without a diluent (as free base) or else be formed in situ from a corresponding salt and a base. They are preferably used without a diluent. For this, they can, for example, be extracted with a solvent of low polarity, such as dichloromethane or diethyl ether, from a neutralized solution of one of their salts and be isolated by evaporating the solvent (EP-A-0 024 200).

The salts of the malondiimidates (I) used are preferably the dihydrochlorides.

The process according to the invention is preferably used for the preparation of (4,6-dimethoxypyrimidin-2-yl)methyl ketones, by using dimethyl malondiimidate ($R^1=Me$) as malondiimidate (II).

The β-keto esters (III) used are preferably acetoacetic esters ($R^2=Me$), 3-oxopentanoic esters ($R^2=Et$) or benzoylacetic esters ($R^2=Ph$).

Preferred β-keto esters are the methyl and ethyl esters ($R^3=Me, Et$).

The process according to the invention is advantageously carried out in an inert solvent, such as, for example, toluene or xylene. The reaction temperature is advantageously 50 to 150° C.

The examples below illustrate how the process according to the invention is carried out, but are not intended to impose any limitation.

EXAMPLE 1

1-(4,6-Dimethoxypyrimidin-2-yl)propan-2-one (I, $R^1=R^2=Me$)

A solution of dimethyl malondiimidate (6.51 g, 0.61 mol) in xylene (20 ml) was added to a solution, heated to 135° C. (reflux), of methyl acetoacetate (5.92 g, 50 mmol) in xylene (80 ml) over the course of 135 min in a flask fitted with reflux condenser and water separator such that the reaction mixture continued to reflux. After refluxing for a further 90 min, the reaction mixture was firstly filtered at 70° C., the filtrate was farther cooled to room temperature and then evaporated. The orange-brown oily crude product (8.35 g) was purified by column chromatography with hexane/ethyl acetate (v:v=5:1) over silica gel 60.

Yield: 5.56 g (56%, based on the diimidate) of a yellowish oil, which solidifies after a while.

$^1$H NMR (CDCl$_3$): δ=5.92 (s, 1H); 3.91 (s, 6H); 3.86 (s, 2H); 2.27 (s, 3H). The spectrum additionally has signal for the enol form.

EXAMPLE 2

1-(4,6-Dimethoxypyrimidin-2-yl)butan-2-one (I, $R^1$=Me, $R^2$=Et)

The procedure was as described in Example 1, except that the methyl acetoacetate was replaced by an equivalent amount of methyl 3-oxopentanoate, the addition period was 150 min with an after-reaction time of 120 min, and the reaction mixture was filtered at 90° C.

Yield: 6.7 g (64%) of a yellow oil.

$^1$H NMR (CDCl$_3$): δ=5.91 (s, 1H); 3.91 (s, 6H); 2.59 (q, 2H); 1.09 (t, 3H). The spectrum additionally has signals for the enol form.

EXAMPLE 3

1-(4,6-Dimethoxypyrimidin-2-yl)propan-2-one (I, $R^1$=$R^2$=Me)

The procedure was as described in Example 1, except that the methyl acetoacetate was replaced by an equivalent amount of ethyl acetoacetate, the addition time was 130 min with an after-reaction time of 280 min, and the reaction mixture was filtered at 90° C.

Yield: 5.18 g (54%, based on the diimidate) of a yellowish oil, which solidifies after a while.

The invention claimed is:

1. A process for the preparation of a (pyrimidin-2-yl) methyl ketone of the formula:

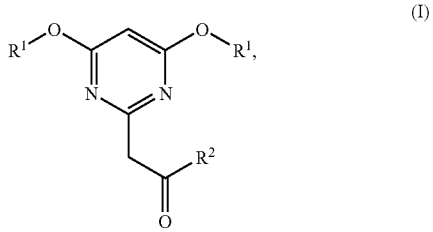

(I)

in which $R^1$ is in each case a $C_{1-10}$-alkyl group, a $C_{3-8}$-cycloalkyl group, an allyl group or an aryl-$C_{1-4}$-alkyl group, and $R^2$ is a $C_{1-10}$-alkyl group or an aryl group, comprising reacting a malondiimidate of the formula:

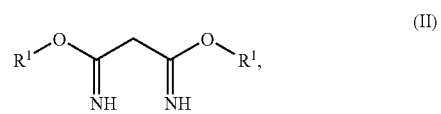

(II)

in which $R^1$ has the meaning given above, with a β-keto ester of the formula:

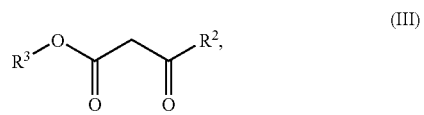

(III)

in which $R^2$ has the meaning given above, and $R^3$ is a $C_{1-10}$-alkyl group.

2. A process according to claim 1, wherein the water formed during the reaction is removed from the reaction mixture during the reaction.

3. A process according to claim 2, wherein the malondiimidate (II) is prepared in situ from a corresponding salt and a base.

4. The process according to claim 3, wherein the salt of the malondiimidate (II) used is the dihydrochloride.

5. The process according to claim 4, wherein the malondiimidate (II) used is dimethyl malondiimidate.

6. The Process according to claim 5, wherein the β-keto ester (III) used is an acetoacetic ester, 3-oxopentanoic ester or benzoylacetic ester.

7. The process according to claim 2, wherein the malondiimidate (II) is prepared in situ from a corresponding salt and a base.

8. The process according to claim 7, wherein the salt of the malondiimidate (II) used is the dihydrochloride.

9. The process according to claim 1, wherein the malondiimidate (II) used is dimethyl malondiimidate.

10. The process according to claim 2, wherein the β-keto ester (III) used is an acetoacetic ester, 3-oxopentanoic ester or benzoylacetic ester.

11. The process according to claim 1, wherein, in formulae (I) and (II), $R^1$ is methyl.

12. The process according to claim 1, wherein the reaction is carried out in an inert solvent.

13. The process according to claim 1, wherein the solvent is toluene or xylene.

* * * * *